United States Patent [19]
Lam et al.

[11] Patent Number: 5,629,470
[45] Date of Patent: May 13, 1997

[54] TRANSGENIC PLANTS AND PLANT CELLS WITH ENHANCED PATHOGEN RESISTANCE AND RELATED METHODS

[75] Inventors: Eric Lam, East Brunswick; Ron Mittler, Piscataway, both of N.J.

[73] Assignee: Rutgers, The State University of New Jersey, New Brunswick, N.J.

[21] Appl. No.: 375,778

[22] Filed: Jan. 20, 1995

[51] Int. Cl.$^6$ .............................. A01H 5/00; C12N 5/04; C12N 15/82

[52] U.S. Cl. ............... 800/205; 435/69.1; 435/172.3; 435/240.4; 435/320.1; 536/23.7

[58] Field of Search ..................... 800/205, DIG. 9, 800/DIG. 52; 435/69.1, 172.3, 240.4, 320.1; 536/23.7

[56] References Cited

U.S. PATENT DOCUMENTS

| | | | |
|---|---|---|---|
| 5,034,322 | 7/1991 | Rogers | 435/172.3 |
| 5,231,019 | 7/1993 | Paszkowski | 435/172.3 |

OTHER PUBLICATIONS

Cell, vol. 77, 565–577, May 20, 1994, "Arabidopsis Mutants Stimulating Disease Resistance Response", Robert A. Dietrich, Terrence P. Delaney, Scott J. Uknes, Eric R. Ward, John A Ryals and Jeffery L. Dangl.

Biotechnology in Plant Disease Control, pp. 139–156, 1993, Wiley–Liss, Inc., "The Role of Cell Wall Degrading Enzymes in Fungal Disease Resistance," Chapter 8, Karen Broglie, Richard Brogile, Nicole Benhamou, Ilan Chet.

"The Molecular Biology of Systems Acquired Resistance", Mechanisms of Plant Defense Responses, 422–432, 1993, K. Lawton, S. Ukness, L. Friedrich, T. Gaffney, D. Alexander, R. Goodman, J.P. Metraux, H. Kessmann, P. Ahl Goy, M. Gut Rella, E. Ward, J. Ryals.

"Environmental Risks in Agricultural Biotechnology", Chemistry and Industry, Jan. 1994, Peter Kareiva, John Stark, 52–55.

Nucleic Acids Research, vol. 15, No. 8, 1987 "The 5'–Leader Sequence of Tobacco Mosaic Virus RNA Enhances The Expression of Foreign Gene Transcripts in vitro and in vivo" pp. 3257–3273, D. Gallie, D.Sleat, J. Watts, P. Turner, M. Wilson.

Bio/Technology, vol. 12, Sep. 1994, pp. 919–923, "Herbicide Resistant Turfgrass (Agrostis Palustris Huds.) By Biolistic Transformation", C. Hartman, L. Lee, P. Day, N. Turner.

Cell, vol. 76, 419–422, Feb. 11, 1994, "Plant Disease Resistance Genes in Signal Perception and Transduction" C. Lamb.

Science, vol. 262, 26 Nov. 1993, pp. 1432–1436, "Map–Based Cloning of a Protein Kinase Gene Conferring Disease Resistance in Tomatoe", G. Martin, S. Brommonschenkel, J. Chunwongse, A. Frary, M. Ganal, R. Spivey, T. Wu, E. Earle, S. Tanksley.

Science, vol. 265, 23 Sep. 1994, pp. 1804–1805, "Mapping The Sequence of Disease Resistance," Plant Genetics, Anne Simon Moffat.

Proc. Natl. Acad. Sci. USA, vol. 91, pp. 9367–9371, Sep., 1994—Biochemistry, "Photoactive Mitochondria: In Vivo Transfer of a Light–Driven Proton Pump into the Inner Mitochondrial Membrane of Schizosaccharomyces Pombe" Astrid Hoffmann, Volker Hildebrandt, J. Heberle, Georg Buldt.

Bioworld Today, vol. 5, No. 186, Sep. 26, 1994, "Plant Genes That Fight Viruses, Bacteria, Fungi to Standstill Discovered, Sequenced" David Left, Science Editor.

Jr. of Bacteriology, Mar. 1993, pp. 1555–15560, vol. 175, No. 6 "Mechanism of Light—Dependent Proton Translocation by Bacteriorhodopsin" Mark P. Krebs and H. Gobinp Khorana.

Jr. of Biological Chemistry, vol. 262, No. 19 (1987) "Structure—Function Studies on Bacteriorhodopsin" Michael Nassal, Tatsushi Mogi, Sadashiva Karnik and Gobind Khorana.

Dixon et al (1990) Annu. Rev. Plant Physiol Plant Mol Biol 41:339–367.

Steffens et al (1989) Planta 177:160–168.

Fromm et al (1990) Bio/Technology 8:833–839.

*Primary Examiner*—Douglas W. Robinson
*Assistant Examiner*—Elizabeth F. McElwain

[57] ABSTRACT

Provided by this invention are transgenic higher plants and cells thereof which have been transformed with the bacterioopsin (bO) gene to provide greater resistance to pathogen attack. Also, provided are bO vectors for forming the transgenic plants and cells thereof. Additionally, a method for enhancing the resistance of higher plants and cells thereof by attack by one or more pathogens is provided.

20 Claims, 13 Drawing Sheets

EL-301

RM-102

RM-101

EL-RM-XX

PRP: PATHOGEN RESPONSIVE PROMOTOR

EL 301

EL 301

N A M H K F E J B L D O Z

Cab-bO

18S

TRANSGENIC PLANTS AND PLANT CELLS WITH ENHANCED PATHOGEN RESISTANCE AND RELATED METHODS

FIELD OF INVENTION

This invention relates to transgenic higher plants and transgenic cells thereof wherein the transgenic cells have been transformed with a bacterial gene encoding bacterio-opsin (bO). The transgenic plants formed show an enhanced resistance to withstand pathogenic attack. Additionally, the invention provides a method to enhance resistance in higher plants to pathogenic attack.

BACKGROUND OF INVENTION

A great deal of damage is done to higher plants, including crop plants, by pathogenic organisms. Plants are known to have certain natural defenses against pathogens. However, there is often an inability of the plants to recognize the pathogen to cause the defenses of the plants to be induced.

There is great economic loss caused by pathogenic attack against higher plants in which the natural defenses of plants are inadequate or fail to respond and defend the plants against damage by pathogens.

As used herein, the term "higher plant" refers to a multicellular differentiated organism that is capable of photosynthesis, such as angiosperms and multicellular algae. The term does not include microorganisms, such as bacteria, yeast, and fungi. The term "plant cell" includes any cell derived from a plant; this includes undifferentiated tissue such as callus, as well as plant seeds, pollen, or plant embryos.

It is known that higher plants have a general plant defense mechanism against plant pathogens. At the present, the mechanism that triggers the activation of plant defense mechanisms and induces systemic resistance is not known. It is known that pathogenic attack can cause in plants the synthesis of high levels of Pathogenesis-Related (PR) proteins. Among these, PR-1 is usually synthesized in response to viral attack; PR-2 encodes a β-1,3-glucanase, which may serve as an anti-bacterial/fungal enzyme; PR-3 encodes an anti-fungal enzyme, chitinase (Linthorst, 1991); Phenylalanine ammonia-lyase (PAL), a key enzyme in the phenylpropanoid pathway that is involved in the biosynthesis of phenolic compounds (Bowles, 1990).

Transgenic plants of this invention contain much higher levels of PR proteins and salicylic acid (SA) than corresponding wild-type plants, and accumulate UV-fluorescence compounds (accumulation of UV fluorescence compounds is a well documented anti-microbial process that is part of the plant defense mechanism). Higher endogenous levels of SA are known to function as a signal for systemic acquired resistance against a broad spectrum of pathogens (including virus, bacteria and fungi) in plants. Upon challenge with viral and bacterial pathogens, it has been found that the transgenic plants provided by this invention show heightened disease resistance, similar to systemic acquired resistance.

The following is a list of designations used herein and the designations have the following definitions:
bO gene—bacterio-opsin gene
Cab-t—chlorophyll a/b binding protein transit peptide
GUS—β-glucuronidase coding region
HR—Hypersensitive Response
NOS—nopaline synthase gene
Ω—synthetic omega translation enhancing sequence
PCR—polymerase chain reaction
PR—Pathogenesis Related Proteins, for example, PR-1, PR-2 and PR-3
SA—salicylic acid
SAR—systemic acquired resistance
TMV—tobacco mosaic virus
TNV—tobacco necrosis virus
WT—wild-type plants (plants which are not transgenic)

SUMMARY OF THE INVENTION

Provided by this invention is a process to provide higher plants with enhanced resistance to pathogenic attack by one or more plant pathogens by transforming cells of higher plants with the bO gene. The bO gene is present in the bacteria *Halobacterium halobium*. The plants can be transformed using various means including using vectors, such as binary vectors, as illustrated in FIG. 1.

Provided also are higher plant cells transformed to encode the bO gene, resulting in enhanced resistance to the pathogenic attack by one or more plant pathogens.

Also, provided are transgenic higher plants which encode the bO gene resulting in higher plants having enhanced resistance to pathogenic attack by one or more plant pathogens.

Provided also are bO vectors which can be used to transform the cells of higher plants according to the invention.

BRIEF DESCRIPTION OF THE DRAWINGS

FIG. 7A—Control WT leaf

FIG. 7B—The same WT leaf showing no occurrence of UV-fluorescence compounds

FIG. 7C—Transgenic EL-301 leaf with spontaneous lesions

FIG. 7D—The same EL-301 leaf showing accumulation of UV-fluorescence.

FIG. 8A (a) Control WT tobacco infected with TMV

FIG. 8B (b) Equivalent leaf of a transgenic (R1 progeny of EL 301A) plant infected with TMV FIG. 8C (c) Control WT tobacco infected with TNV.

FIG. 8D (d) Equivalent leaf of a transgenic (R1 progeny of EL 30 1A) plant infected with TNV.

FIG. 1 for vector description) plants, indicating an increased disease resistance compared with the corresponding wild-type plants (WT Samsun, WT SR1). No bacterial growth was found in mock-inoculated plants. The data presented are the mean and standard deviation from five individual leaves. Conditions for pathogen infection and analysis are described in Methods, CFU, colony-forming unit.

DETAILED DESCRIPTION OF THE INVENTION AND ITS PREFERRED EMBODIMENTS

In an illustrative preferred embodiment of the invention, cells of tobacco plants are transformed with the bO encoding gene. The transformed plants show enhanced capability to withstand pathogenic attack.

The bO gene is derived from the bacterium $Halobacterium\ halobium$. The bO gene is described in an article by Nassal et al., 1987.

Figure 1:
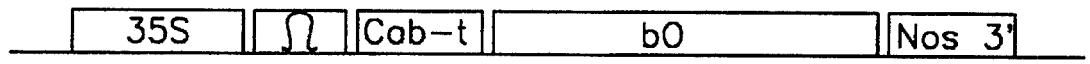
FIG. 1 are diagrams showing: (1) the binary vector EL-301 having a bO gene segment, a 35S segment which is a promoter fragment (800 base), an "Ω" segment which is the omega translation enhancing segment sequence, and a Cab-t segment which represents Cab-transit peptide; (2) the RM-102 vector which corresponds to the EL-301 vector except it does not have the Cab-transient peptide segment; transgenic plants transformed using these vectors form spontaneous lesions (lesion mimic); (3) RM 101 vector corresponding to EL-301 vector except the bO segment of EL-301 has been replaced with the GUS (β-glucuronidase) coding region, RM-101 is a control vector (this vector when used to transform plants was found to provide plants indistinguishable from control SR-1 plants); and (4) EL-RM-XX vectors for pathogen driven hypersensitive response in transgenic plants; the pathogen-responsive promoter (PRP segment) will cause localized pathogen derived high expression of the bO gene, resulting in the formation of lesions (much like the spontaneous lesions formed on transgenic plants that express high levels of the bO gene).
Figure 1:
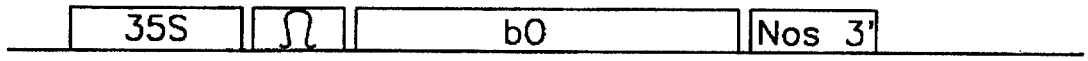
Figure 1:
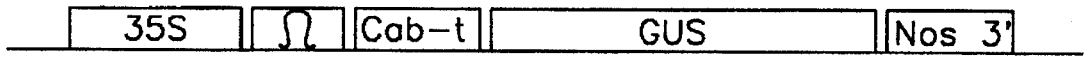
Figure 1:
Figure 1:
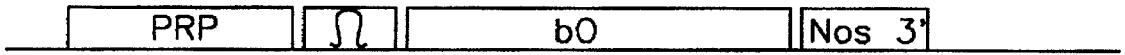

It has been found that the bO gene material can be introduced into the tobacco or other higher plant cell in a vector that can be mobilized into plant cells via $Agrobacterium\ tumefaciens$, such as by a binary vector as shown in FIG. 1. The bO gene material can also be introduced by other known methods, such as by use of a "gene gun".

The vector structure (EL-301) shown in FIG. 1 is as follows:

35S—Ω—Cab-t—bO—Nos 3'

The vector was assembled using known methods of biology including restriction digests, ligation and PCR. The nucleotide sequences of the designated vectors were determined to confirm the published structures.

Other bO vectors shown in FIG. 1 are RM-102 (Cab-t segment was deleted from the structure of EL-301 vector) and RM-101 (bO gene segment of EL-301 was replaced with GUS segment) were likewise assembled. EL-RM-XX vectors (35S segment of EL-301 and RM-102 will be replaced with promoters known to be activated upon pathogen attack). They have the following structures:

RM-102

35S—Ω—bO—Nos 3'

RM-101

35S—Ω—Cab-t—GUS—NOS 3'

EL-RM-XX (1) PRP—Ω—Cab-t—bO—Nos 3'

(2) PRP—Ω—bO—Nos 3'

The backbone vectors were purchased through commercial sources (SK pBluescript from Stratagene and pBI100 series from Clontech). The following is a description of other sources and methods used to obtain the different components of the construct:

a. 35S promoter of cauliflower mosaic virus was obtained by restriction digest from the pBI121 vector.

b. Chlorophyll A/B binding protein-transit peptide was obtained by PCR from total soybean genomic DNA.

c. Omega translation enhancer sequence was obtained by PCR based on published sequence.

d. bO gene was subcloned from a plasmid containing an artificial gene encoding the bO protein (given by Dr. Mark P. Krebs of Dr. Gobind Khorana's laboratory).

e. termination signal was obtained by restriction digest of the pBI112 1 vector.

f. GUS open reading frame was obtained by restriction digest of the pBI121 vector. All portions of the constructs (FIG. 1) were initially cloned into pBluescript and sequenced and the final construct was then mobilized into the pBI100 backbone binary vector.

In illustration, the EL-301 bO gene vector structure was constructed by the following procedure: The chlorophyll a/b transit peptide (Cab-t) coding region was amplified by polymerase chain reaction from total genomic soybean DNA and fused to the bO gene (gift of G. Khorana, Massachusetts Institute of Technology, Camridge, Mass.; Nassal et al., 1987). The Cab-t/bO fusion gene was then fused to a synthetic Ω translation enhancing sequence and inserted downstream from the cauliflower mosaic virus 35S promoter (FIG. 1). The 35S—Ω—Cab-t—bO—Nos (noapline synthase) 3' construct was inserted into a T-DNA pBI100 backbone plasmid (Clontech) and mobilized into tobacco (Nicotiana tabaccum cv Samsun NN) plants via Agrobacterium tumefaciens mediated transformation (Fraley et al., 1985). Individual transformants were screened for the expression level of the bO transgene by RNA gel blot analysis. Other bO gene vectors such as EL-301 vector variants can be conducted which are effective in providing enhanced capability by plants to withstand pathogenic attack.

The following is a discussion of biological mechanisms or pathways involved in the increased resistance of higher plants transformed with this invention.

During the HR, the recognition of a pathogen induces a rapid cell death process that results in the formation of a zone of dead cells around the site of infection. This HR lesion is believed to inhibit further spread of the pathogen and to generate a signal that activates host defense mechanisms and, in many cases, induces long-lasting systemic resistance to a broad spectrum of pathogens (Ross, 1961). Induction of such systemic resistance is termed systemic acquired resistance (SAR) and is accompanied by an increase in the rate of synthesis of several pathogenesis-related (PR) proteins and the accumulation of salicylic acid (SA) (Malamy et al., 1990; Metraux et al., 1990; Ward et al., 1991). In certain instances, however, at least some of these host defense mechanisms can be activated in the absence of a pathogen. These include a variety of maize, barley, tomato, and arabidopsis mutants that develop spontaneous lesions similar to lesions caused by a pathogen attack. These mutants are often teethed "disease lesion mimics" and are thought to develop lesions that resemble necrotic disease symptoms or HR lesions in the absence of a pathogen (Neuffer and Calvert, 1975; Hoisington et al., 1982; Walbot et at., 1983; Wolter et al., 1993). The occurrence of these mutants, especially mutants that spontaneously develop lesions that resemble HR lesions (HR-type lesions), provides evidence for the involvement of a genetically defined pathway for cell death during the HR. Thus, plants may contain a pathway for cell death that can be spontaneously activated in the absence of a pathogen.

It has been demonstrated recently that in some of the Arabidopsis lesion mimic mutants the appearance of HR-type lesions is also coordinated with activation of host defense mechanisms, such as PR protein induction, phytoalexin production, and accumulation of SA (Dietrich et al., 1994; Greenberg et al, 1994). Interestingly, as many as 60 to 80 different loci specifying a lesion mimic phenotype were identified in maize (Pryor, 1987; Walbot, 1991). Such a large number of different loci may suggest that the spontaneous activation of the HR cell death program is not only the outcome of mutations in a specific pathogen recognition gene but may also be the result of mutations that alter cellular homeostasis. The unbalanced biochemical state induced by such a mutation may be misinterpreted by host cells for a pathogen infection, resulting in the triggering of the HR cell death pathway (Dietrich et al., 1994). Additional support for this model stems from reports that the pertubation of the ubiquitin-dependent protein degradation pathway (Bachmair et al., 1990; Becker et al., 1993) and expression of certain transgenes in tobacco plants (Takahashi eta., 1989; Elkind et al., 1990) induce lesion formation. However, in addition to lesion formation, these plants exhibit several other phenotypes, including abnormal or suppressed growth. This may indicate that perturbing cellular homeostasis by the expression of these transgenes and by inhibiting the ubiquitin system may have resulted in a general nonspecific effect on cellular metabolism. In addition, none of the genes responsible for the "disease lesion mimic" phenotype has been cloned.

By this invention, the expression of the bacterial proton-channel bO gene illustrated in transgenic tobacco results in a phenotype that is very similar to the "disease lesion mimic" mutants. HR-type lesions were formed and multiple defense mechanisms were activated in the absence of a pathogen. Transgenic plants expressing the bO gene also exhibited heightened disease resistance against certain viral and bacterial pathogens (FIGS. 8A–8D and FIGS. 9A–9C). However, in contrast to other transgenes that induce lesions, bO-expression did not result in abnormal or suppressed growth except in cases of very high overexpression.

RESULTS

Figure 2A:
FIG. 2A shows the structure of EL binary vector.
Figure 2B:
FIG. 2B shows screening of transgenic tobacco plants that express the bO gene using RNA gel blot analysis with a probe to the bO gene (top panel) and with a probe to the 18S ribosomal RNA (bottom panel, as control).
Figure 2B:

Expression of bO gene in higher plants has been shown to result in a "disease lesion mimic" phenotype. A gene was introduced from Halobacterium halobium encoding bO (Krebs and Khorana, 1993) into tobacco (Nicotiana tabacum cv. Samsun NN). Functioning as a light-driven proton pump that utilizes a different light spectrum from that used by the photosynthetic apparatus of higher plants, the bO proton-pump may increase the photosynthetic capacity of these plants when supplied with its chromophore retinal. In order to direct the bO protein into the thylakoid membrane, the bO gene was fused to the soybean chlorophyll a/b binding protein transit peptide (FIG. 1, EL 301, Cab-t). Different families of transgenic tobacco plants were generated that vary in the level of expression of the Cab-t/bO fusion gene, presumably due to insertion of the gene into different regions of the plant genome and/or different copy numbers of the transgene (FIG. 2B). Transgenic plants expressing the bO gene were found to contain detectable levels of the mature bO protein indicating that the Cab-t/bO fusion protein was processed to its mature form in plants.

Figure 3A:
FIG. 3A shows a leaf of a lesion mimic phenotype of a high expressor demonstrating the appearance of spontaneous lesions on a tobacco plant leaf.
Figure 3B:
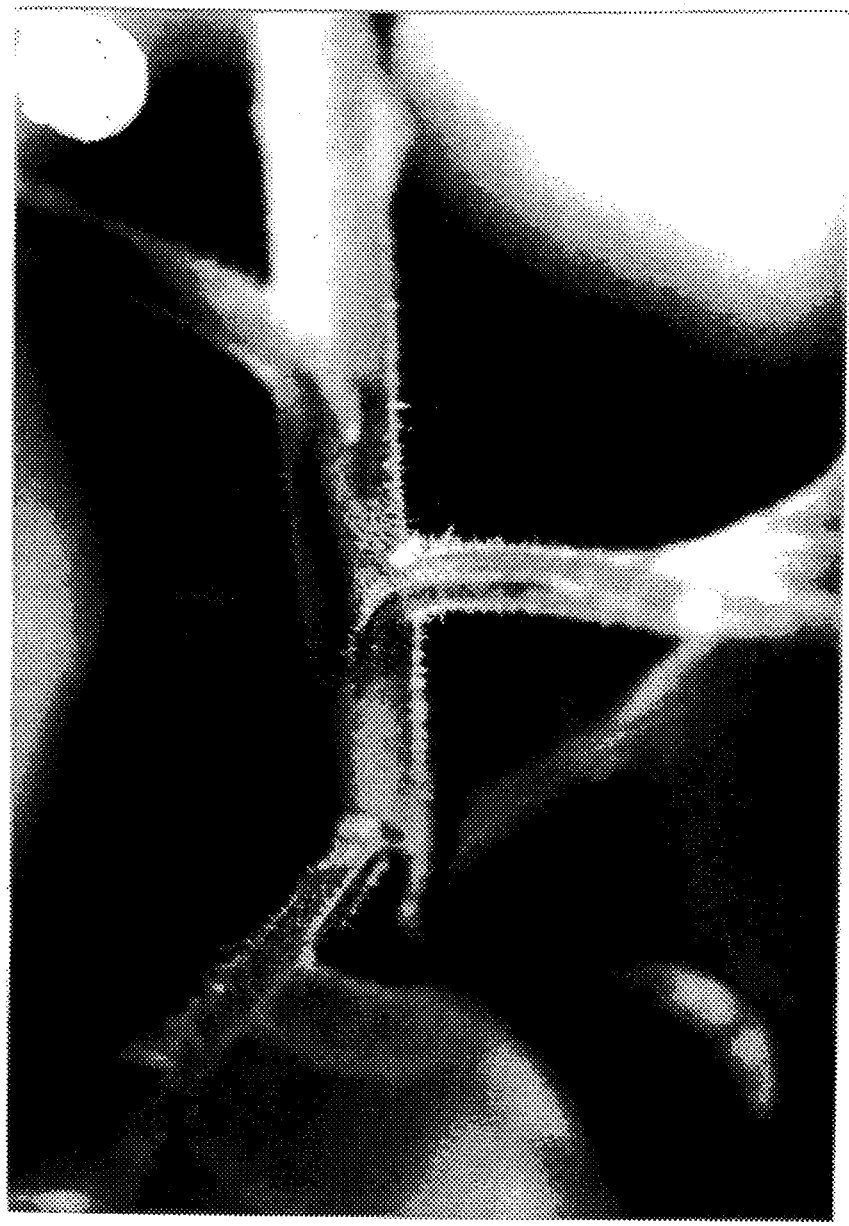
FIG. 3B shows a stem of a lesion mimic phenotype of a high expressor demonstrating the appearance of spontaneous lesions on a tobacco plant stem.

Introduction of the bO gene into the tobacco genome produced a phenotype very similar to that of the "disease lesion mimic" mutants (FIGS. 3A and 3B). Transgenic tobacco plants expressing the bO gene developed distinct HR-type lesions on leaves and stems. However, these plants did not exhibit growth or developmental abnormality. The number and size of spontaneous lesions were roughly correlated with the expression level of the bO transgene.

Figure 4:
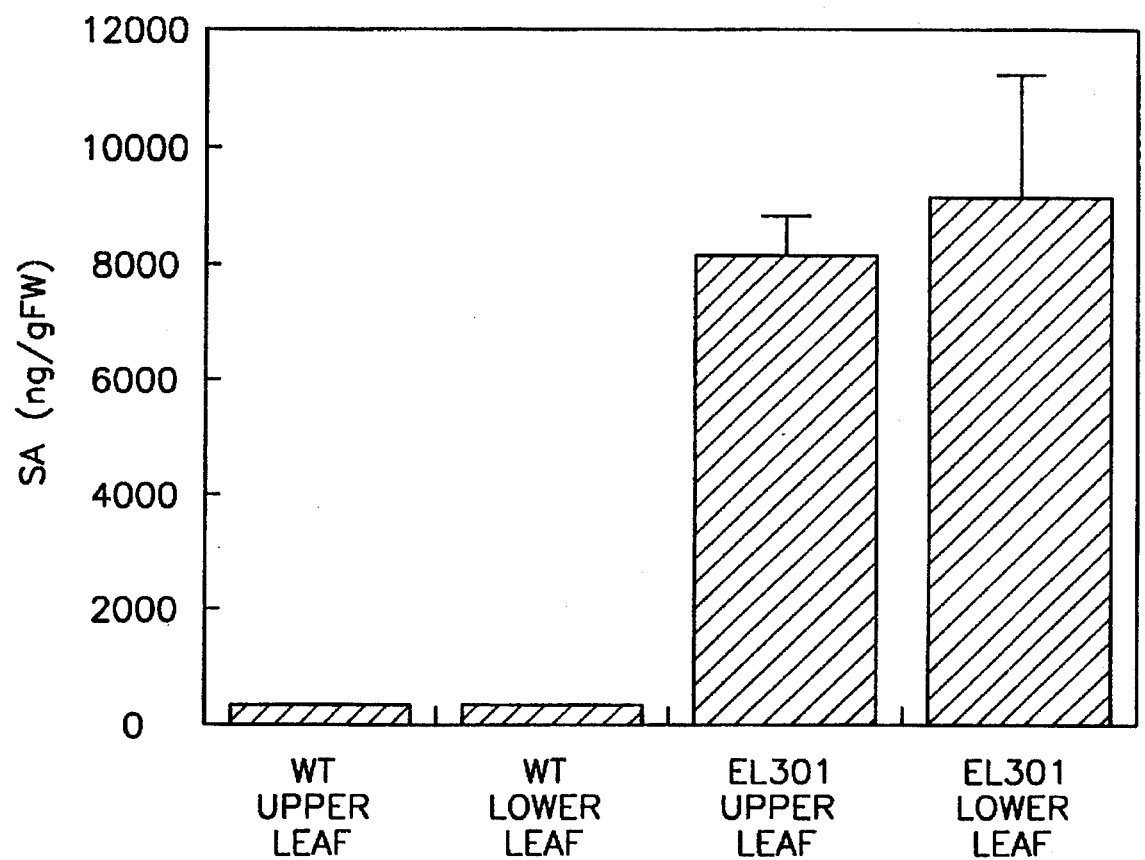
FIG. 4 is bar graph having lanes 1–4 showing SA levels in leaves of control wild-type (WT) and transgenic (EL301) plants expressing the bO gene. Plant material was collected from upper (no lesions) and lower (with lesions) leaves of 5-week-old bO expressing plants and wild-type plants. Leaf tissue (0.3 g) was analyzed for total SA content as described in Methods section appearing below. The data presented are the mean and standard deviation of five individual samples gFW, grams fresh weight, of tissue.
Figure 5:
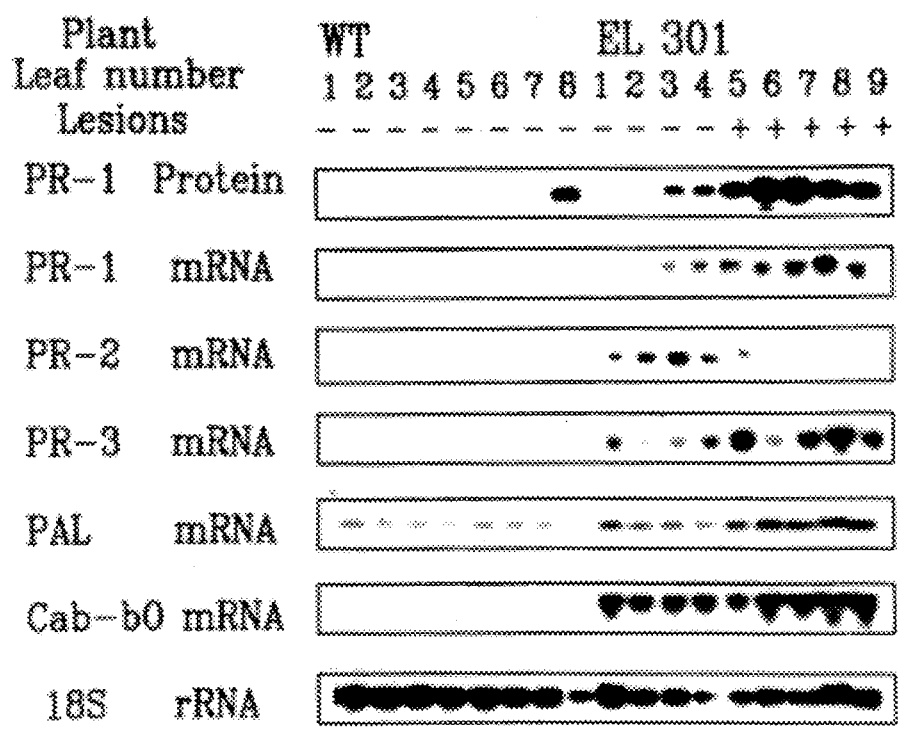
FIG. 5 shows expression of genes encoding PR proteins and phenylalanine ammonia-lyase (PAL) in transgenic tobacco plants expressing the bO gene. Expression of PR proteins and PAL was compared between various leaves of a greenhouse grown wild-type plant (WT, 1 to 8, top to bottom) and a transgenic tobacco plant expressing the bO gene (EL 301A, 1 to 9, top to bottom). Occurrence of spontaneous lesions is indicated (+) on the bottom leaves of the bO-expressing transgenic plant. Leaves obtained from top (leaf number 1) to bottom (leaf number 8 or 9) of a wild-type (WT) and a transgenic (RI progeny of EL 301) Samsun NN greenhouse-grown plants were analyzed by RNA gel blots and immunoblots. Total RNA (30 µg) was loaded in each lane, and hybridization was conducted with the probes indicated at left. PR-1, PR-2 and PR-3 transcripts were detected with the corresponding tobacco cDNAs as probes and the level of PAL transcript with a corresponding parsley cDNA as a probe. PR-1 protein was detected via immuno-blot with a monoclonal anti-PR-1 antibody.
Figure 6:
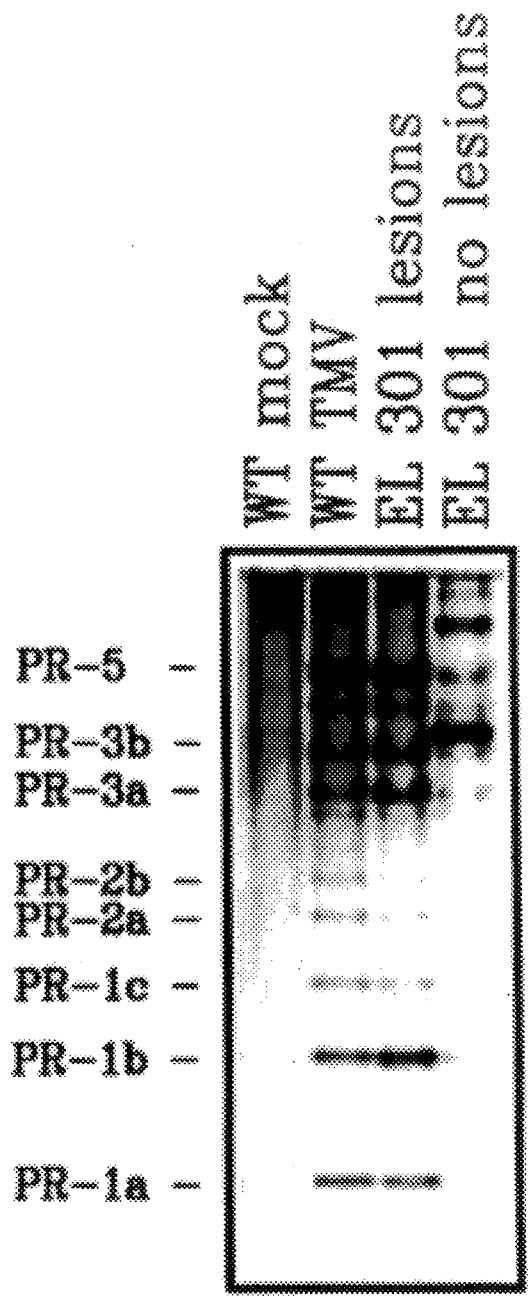
FIG. 6 is a protein gel analysis showing occurrence of PR proteins in the intercellular fluid of leaf tissue with spontaneous lesions (EL 301, with lesions) or without lesions (EL 301, no lesions) from bO-expressing plants. The level of PR proteins is compared with the intercellular fluid from mock infected (WT mock) and TMV infected (WT TMV) wild-type Samsun NN plants. Intercellular fluid was collected and analyzed according to Lawton et al. (1993), The molecular biology of systemic acquired resistance. In Mechanisms of Plant Defence Responses, B. Fritig and M. Legrand, eds (Dordrecht, Netherlands, Kluwer Academic Publishers), pp. 422–432.
Figure 7A:
FIG. 7A–FIG. 7D show the accumulation of UV-fluorescence compounds in leaves of an EL-301 transgenic plant.
Figure 7B:
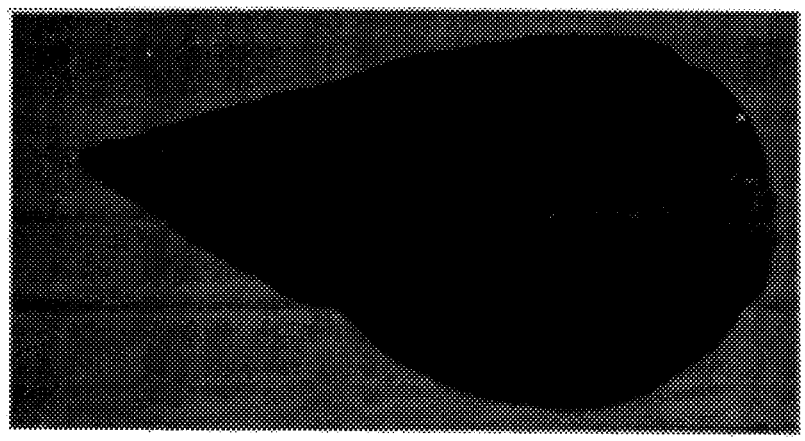
Figure 7C:
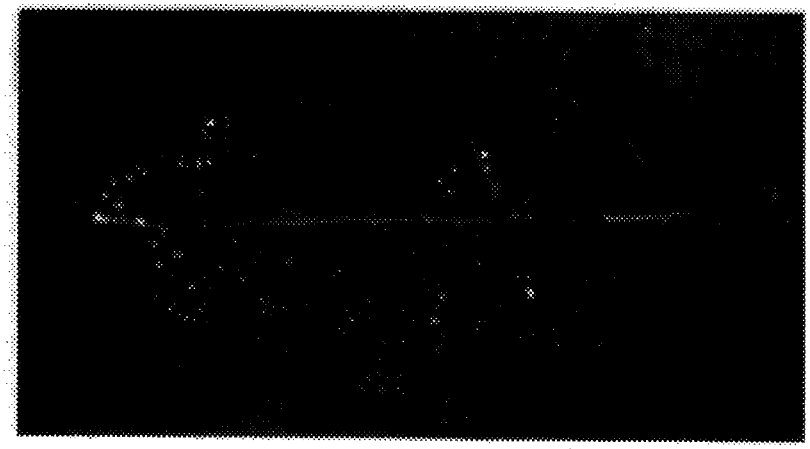
Figure 7D:
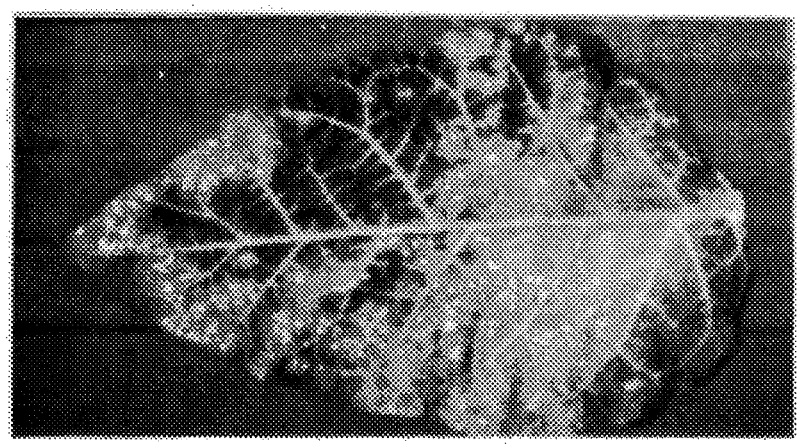
Figure 8A:
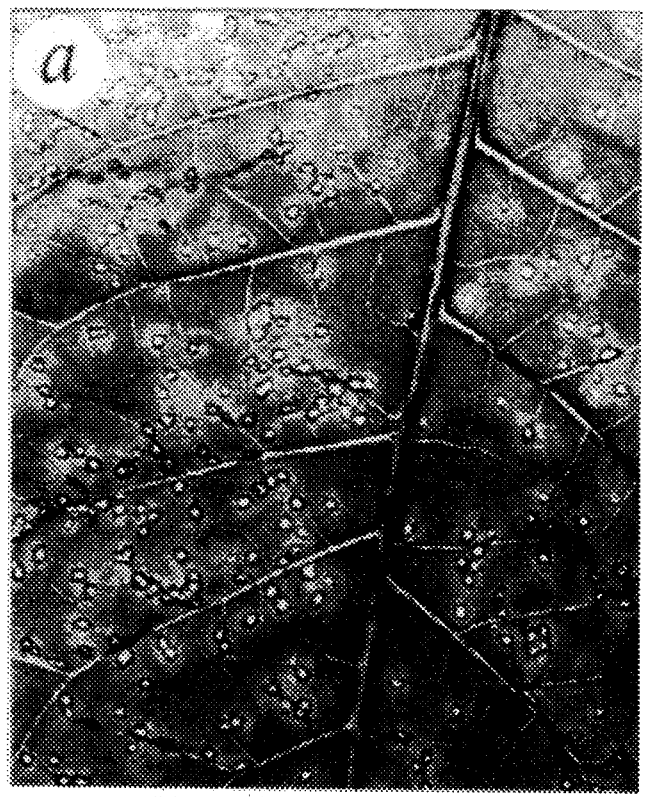
FIG. 8A–FIG. 8D are photographs of leaves of tobacco plants showing heightened disease resistance of transgenic plants expressing bO to TMV and TNV infection.
Figure 8B:
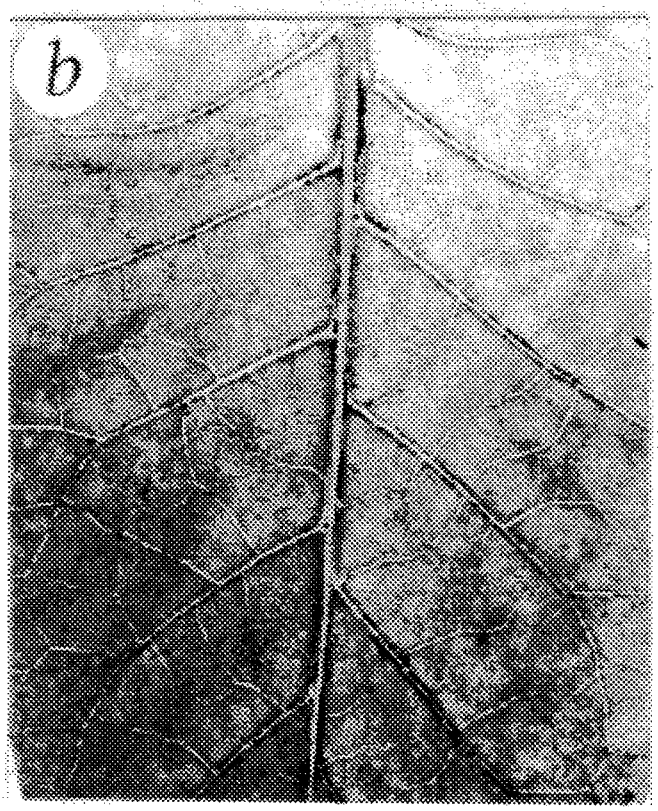
Figure 8C:
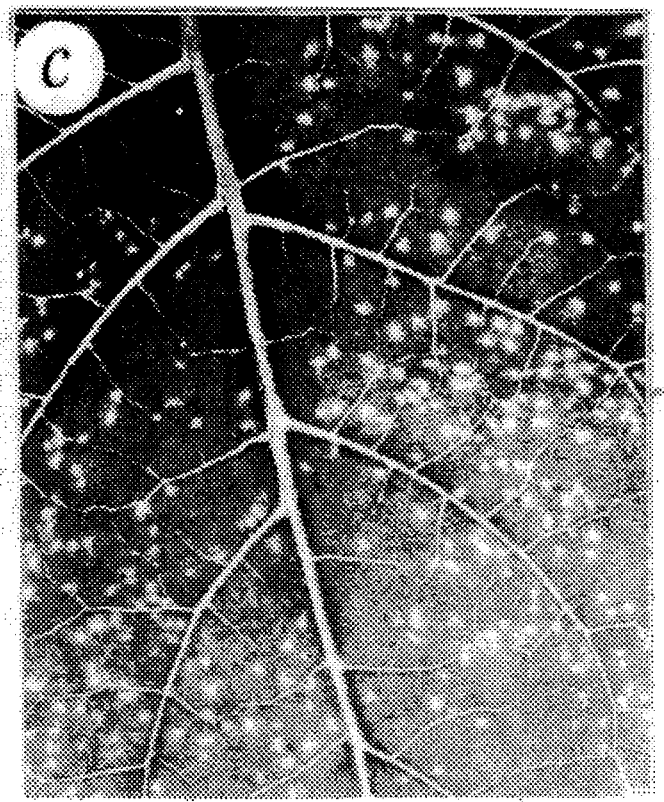
Figure 8D:
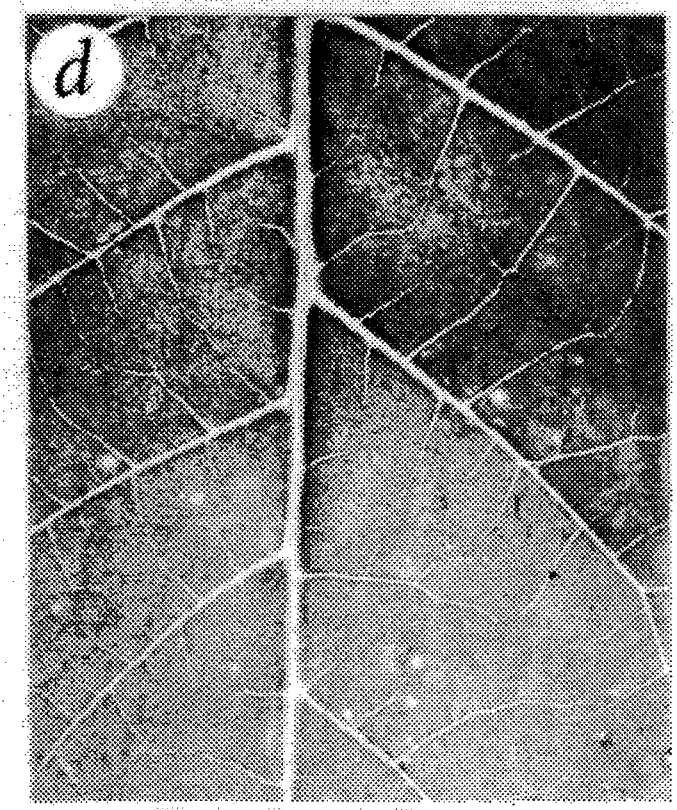

Formation of Spontaneous Lesions is Coordinated with Activation of Host Defense Mechanisms Since the appearance of spontaneous lesions in the transformed plants indicated that the introduction of the bO gene into the tobacco genome may have activated some general plant defense mechanisms, the expression levels of several PR proteins were examined. Transgenic plants expressing the bO gene produced high levels of PR proteins in a constitutive manner both in tissue culture and under normal growth conditions (FIG. 5). Among these: PR-1 is usually synthesized in response to viral attack; PR-2 enclodes a β-1,3-glucanase which may serve as an anti-bacterial/fungal enzyme; and PR-3 encodes an anti-fungal enzyme, chitinase (Linthorst, 1991). Phenylalanine ammonia-lyase (PAL), a key enzyme in the phenylpropanoid pathway involved in the biosynthesis of phenolic compounds (Bowles, 1990), also appeared to increase in its expression level. Several PR proteins were found in the intercellular fluid of leaf tissue from bO-expressing plants (FIG. 6). The pattern of synthesis of these PR proteins was similar to that occurred in TMV-infected Samsun NN wild-type plants, supporting the similarity observed between the spontaneous lesions and TMV-induced lesions. This similarity also suggests that expression of the bO gene may trigger the same host defense mechanism that is naturally activated by a TMV infection. In addition, as shown in FIG. 4, both the lower (lesion containing) and upper (no lesions) leaves of bO-expressing plants contained very high levels of SA compared to wild-type tobacco. Since SA is thought to mediate the process of SAR in tobacco (Enyedi et al., 1992), this observation is consistent with a constitutive activation of SAR in bO-expressing plants. Furthermore, the appearance of spontaneous lesions was accompanied by accumulation of autofluorescent compounds around the lesions and in the cell walls of collapsed cells within the lesions (FIGS. 7A–7D). This may be indicative of cross-linked phenolics that serve to strengthen cell walls against an invading pathogen (Dietrich et al., 1994). Accumulation of auto fluorescent material did not occur in response to wounding by dry ice, suggesting that the bO-derived lesions were not simply the result of cellular injury but rather appear to be the outcome of HR activation. Thus, introduction of the bO gene into the tobacco genome has been shown to result in the spontaneous activation of several components of the plant defense mechanism against an invading pathogen. These included the triggering of an HR-type cell death response in the absence of a pathogen, induction of several PR proteins, accumulation of autofluorescent material and high levels of SA. Activation of host defense mechanisms in the absence of a pathogen is similar to the activation of defense mechanisms in some of the "disease lesion mimic" mutants recently described in Arabidopsis (Greenberg et al., 1994; Dietrich et at., 1994).

Induction of Systemic Resistance Against Viral and Bacterial Pathogens

Figure 9A:
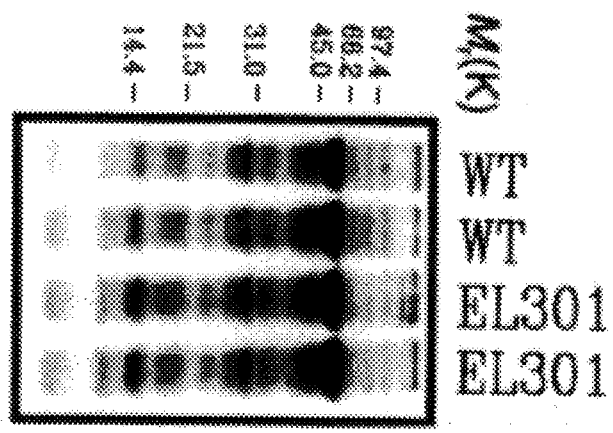
FIG. 9A is a protein gel and FIG. 9B is a corresponding immuno-blot probed with an anti-TMV coat protein serum, demonstrating inhibition of TMV replication in the infected leaf of two individual bO expressing plants compared to two WT plants.
Figure 9B:
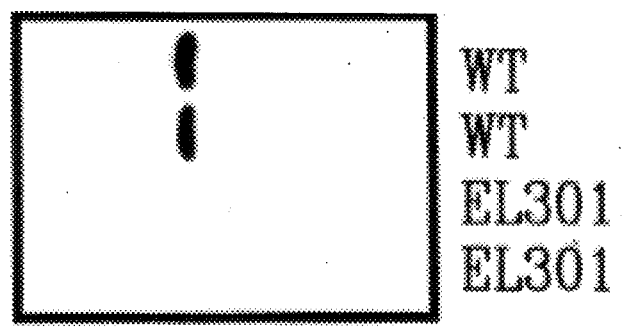

Several of the "disease lesion mimic" mutants exhibited a heightened disease resistance against a variety of pathogens (Wolter et al., 1993; Greenberg et al., 1994; Dietrich et at., 1994). To ascertain whether the constitutive activation of plant defense mechanisms in bO-expressing plants confers disease protection, bO-expressing plants were challenged with TMV and tobacco necrosis virus (TNV). Transgenic tobacco plants expressing the bO gene developed very few HR lesions in response to a TMV challenge and successfully blocked TNV necrotic symptoms (FIGS. 8A–8D). These results are very similar to the response of SAR-induced tobacco plants upon subsequent pathogen infection (Ross, 1961; Ward et al., 1991). Thus, the formation of few HR lesions upon TMV challenge and the blocking of TNV necrotic symptoms are indicative of a heightened disease resistance state induced by expression of the bO gene. Further testing was done on whether the formation of only a few HR lesions on the infected leaf of bO-expressing plants was the outcome of successful inhibition of virus replication. As shown in FIGS. 9A and 9B, bO-expressing plants were superior to wild-type plants in their ability to block the replication of TMV in the infected leaf. This inhibition of TMV replication may explain the formation of very few HR lesions on plants with induced systemic resistance. The amount of TMV particles in the infected leaves of these plants may be insufficient to trigger the HR response.

Figure 9C:
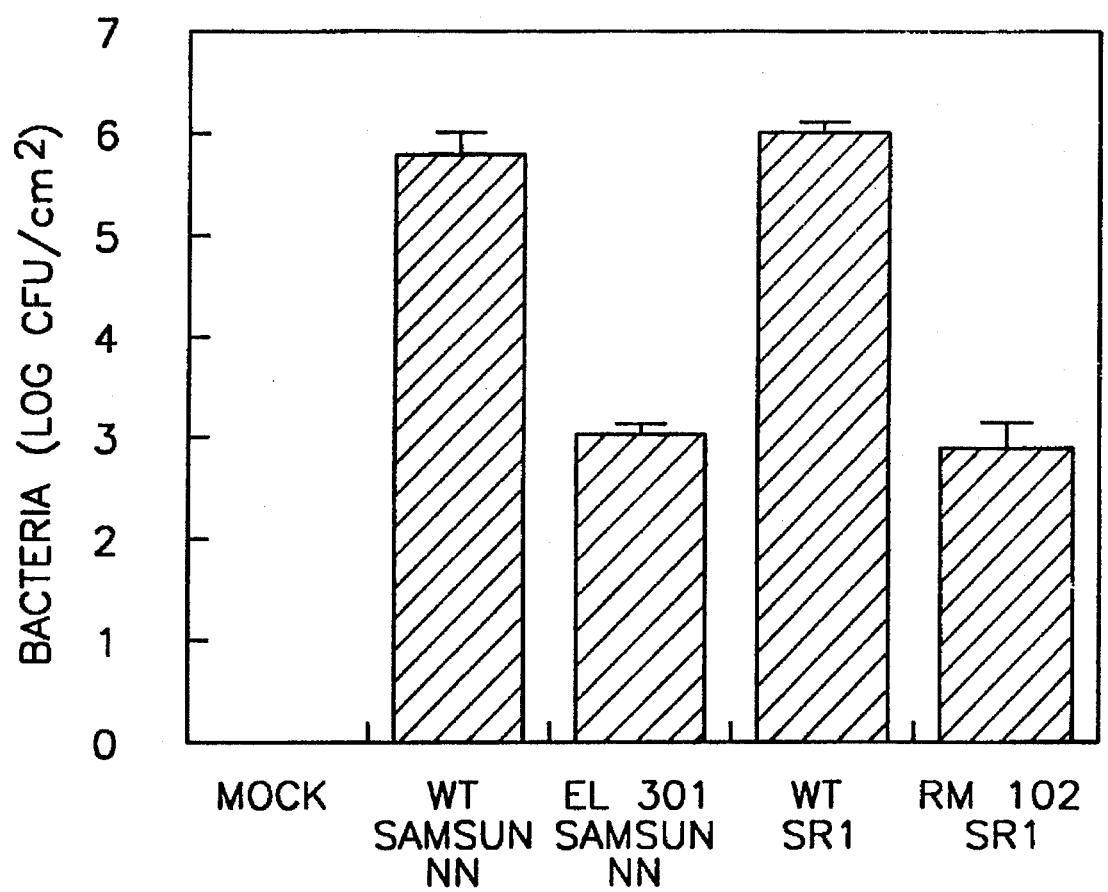
FIG. 9C is a bar graph showing inhibition of $P.s.$ tabaci growth in leaves of bO-expressing Samson (EL 301) and SR1 (RM 102.

The resistance of bO-expressing plants to a bacterial challenge was tested. Transgenic plants expressing the bO gene exhibited a higher degree of resistance to the bacterial pathogen *Pseudomonas syringeae pv. tabaci*. As shown in FIG. 9C, plants expressing the bO gene successfully blocked the growth of bacteria.

These results show that the heightened disease resistance exhibited by bO-expressing tobacco plants is similar to pathogen-induced SAR (Ross, 1961; Ward et al., 1991). This observation suggests that expression of bO in higher plants may be misinterpreted by the plant for a pathogen challenge and that the bO gene action may be similar to some of the "disease lesion mimic" mutations (Greenberg et al., 1994; Dietrich et al., 1994).

Functional Analysis of bO in Plants

Bacterio-opsin is a light driven proton-channel that requires the presence of the chromophore retinal in order to function (Krebs and Khorana, 1993). However, retinal is not thought to be present in higher plants. It is therefore puzzling and unpredictable that the bO protein may have such a dramatic effect on plants. It is possible that the bO protein, when expressed in plants, may still function as a passive proton channel which causes leakage of protons. In order to address the question of bO protein function and to test if this function may involve some proton-pumping properties of the bO protein, a mutated form of bO was expressed that has a single amino acid substitution (Asp to Ala) at position 85 (D85A). This amino acid substitution renders the bO protein incapable of active proton pumping due to an alteration in the charge translocating path through the "proton channel" (Otto et al., 1990). However, this mutant presents the ability to reconstitute with retinal to form a pigment that is very similar to wild-type bacteriorhodopsin. Thus, the protein folding properties of this mutant are likely not affected significantly (Krebs and Khorana, 1993). Transgenic plants expressing this D85A mutant did not develop spontaneous lesions, did not exhibit elevated levels of PR-1 and in contrast to bO-expressing plants did not show heightened disease resistance. However, transgenic plants expressing the D85A mutant did synthesize the mutated bO protein to similar levels as bO-expressing plants. These results suggest that the bO protein may require some active or passive proton-pumping properties for eliciting its lesion mimic phenotype.

It will, however, be understood by those skilled in the art that some mutated forms of bO will be effective to enhance the resistance of higher plants to transgenic attack.

In summary, transgenic plants expressing the bO gene exhibit many characteristics of a "disease lesion mimic" mutant. These include the formation of HR-type lesions, the activation of host defense mechanisms in the absence of a pathogen and the induction of heightened disease resistance similar to pathogen-induced SAR (Greenberg et al., 1994; Dietrich et al., 1994).

Disease lesion mimic mutants were classified into two major groups: initiation mutants and feedback or propagation mutants (Walbot et al., 1983, Dietrich et al., 1994; Greenberg et al., 1994). Initiation mutants form lesions whose growth is determinate, therefore giving rise to lesions with a defined border. These mutants are thought to be defective in regulating the trigger of the HR response, and may either lack a negative regulator of HR activation (a recessive mutation; see 1sd3, 1sd5, Dietrich et al., 1994) or constitutively activate an HR signaling component (a dominant mutation, see 1sd2, 1sd4, Dietrich et al., 1994; Neuffer and Calvert, 1975). Propagation mutants form lesions that spread indeterminately, eventually resulting in the death of the entire leaf. These mutants are presumed to be defective in down-regulating the process of lesion progression (a recessive mutation; see 1sd1, Dietrich et al., 1994; acd1, Greenberg and Ausubel, 1993; acd3, Greenberg et al., 1994). Transgenic plants expressing the bO gene mimic dominant initiation mutants. The dominant nature of the bO transgene also support the assumption that the bO action results in the constitutive activation of a pathogen response signal. Since the bO gene induced spontaneous lesion formation in several different tobacco cultivars (Samsun NN, Xanthi-nc nn and SR1, Mittler and Lam, unpublished data) and in transgenic Arabidopsis plants (Marques and Lam, unpublished data), it is unlikely that it functions by mimicking the infection of a specific pathogen. The expression of the bO gene may therefore affect the activation of the pod pathway at a relatively basic level that is common to different plants.

It has been previously suggested that some of the dominant lesion initiation mutants perturb cellular homeostasis. The resulting unbalanced biochemical state may be misinterpreted by the host cells as a pathogen infection and trigger the HR. Since bacteriorhodopsin is a light driven proton-pump, its expression in higher plants may result in an artificial increase in proton-pumping activity that may perturb the natural ionic homeostasis of the cell. However, plants are presumed to lack retinal which is required for the active pumping of protons. In addition, *Halobacterium halobium* cells deficient in retinal biosynthesis accumulate mature bO protein, suggesting that at least in the bacterial system bO does not cause leakage of protons. However, the expression of the D85A mutant which is incapable of active proton-pumping does not result in a lesion mimic phenotype. This finding suggests that the bO protein may require some properties that involve proton translocation across membranes for eliciting its action as a lesion inducer gene. It may be possible that expression of the bO gene in higher plants alters cellular homeostasis through unbalanced leakage of protons. Such perturbation of cellular homeostasis may in turn trigger a HR pathway. It should be noted that the triggering of the HR in tobacco cells by certain bacterial pathogens requires the activation of a plasma membrane $K^+$ effux/net $H^+$ uptake exchange. In addition, the induction of this altered biochemical balance depends on a plasmalemma $H^+$-pumping ATPase activity (Atkinson and Baker, 1989). Alteration of the proton pumping homeostasis by the bO gene may induce a similar altered biochemical balance causing the spontaneous triggering of a HR pathway.

Since the bO gene functions as a lesion inducer in at least two different plant species and since induction of systemic resistance, similar to SAR, is expected to confer disease protection against a variety of viral, fungal and bacterial pathogens (Lawton et al., 1993), the bO gene may be useful as a general agronomic tool to enhance disease protection in different cultivars against a variety of pathogens. Application of the bO gene may involve screening for transgenic lines that express the bO gene at a moderate level, causing the formation of few spontaneous lesions, yet conferring disease protection. Alternatively, inducible expression of the bO gene by a regulated promoter may allow controlled activation of the plant defense mechanism, thus mimicking the time for which the defense mechanism will be turned on.

RNA Isolation and Analysis

Leaves were collected, frozen in liquid nitrogen and ground to a powder. RNA was then extracted as described by Nagy et al. (1987) and analyzed by northern blots. Northern blots were first hybridized with either the bO or PR and PAL probes and then with a probe for 18S rRNA. Northern blot hybridization and membrane washing were performed using Duralose-UV membranes and quickHyb solution (Stratagene) as suggested by the manufacturer. PR1, PR2 and PR3 transcripts were detected with the corresponding tobacco cDNAs as probes (gift of Dr. D. Klessig), and the level of PAL transcript with a corresponding parsley cDNA as a probe (gift of Dr. K. Hahlbrock).

Protein Isolation and Immunodetection

Immunodetection of PR-1, bO and TMV coat protein was performed by western blot analysis of total leaf protein with a chemiluminescence detection system (Renaissance kit from DuPont). Monoclonal Anti-PR1 antibody was a gift of Dr. D. Klessig, monoclonal anti-bO antibody was a gift of Dr. G. Khorana and anti-TMV coat protein serum was a gift of Dr. N. Turner. Detection of PR proteins in the intracellular fluid of bO-expressing or TMV infected tobacco plants was performed according to the Lawton et al. (1993).

Salicylic Acid Determination

SA was extracted from leaf samples (0.3 g) and quantified by HPLC. Total SA (the sum of free and glucose-conjugated SA) was determined and corrected for SA recovery as previously described (Yalpani et al., 1993).

Pathogen Infection and Analysis

Fully expanded young leaves were infected with equal mounts of TMV strain U1 or TNV strain A, in 5 mM potassium phosphate buffer, pH 7, or mock infected with the same 5 mM phosphate buffer, by gently rubbing the leaves with carborundum. Plants were either kept at 22° C. or 30° C. under continuous light. Lesions were photographed 72 hours post-infection. No lesions developed on mock infected leaves of wild-type and transgenic bO-expressing Samsun NN plants. The progression of lesion formation following a temperature shift from 30° C. to 22° C., of bO-expressing and TMV infected plants, was assayed by measuring ion leakage from leaf discs obtained at different time points following the shift. For each measurement, 5 leaf discs (7 mm diameter) were floated abaxial side up on 6 ml of distilled water for 4 hours at room temperature. Following incubation, the conductivity of the bathing solution was measured with a Model 604 (VWR Scientific) conductivity meter. Measurements for each time point were performed in triplicate. Inoculation of plants with *Pseudomonas syringae pv. tabaci* (ATCC 11528) was performed by infiltrating the leaves with a 1 ml syringe without a needle. Seventy-two hours following infiltration of leaves with bacteria (500 or 15,000 CFU/cm$^{-2}$, in sterile distilled water), the leaves were surface sterilized with 20% bleach/0.1% tween 20 for 1 min and washed three times with sterile distilled water. Leaf discs (10 mm diameter) were taken from the infection site, ground in sterile distilled water, diluted and plated on nutrient agar. No bacterial growth was observed with leaf discs obtained from mock inoculated plants that were infiltrated with sterile water.

EXAMPLE

Construction of an Expression Vector for the Overproduction of Bacterio-opsin in Higher Plants by Agrobacterium Mediated Transformation The construction of the EL301 vector consisted of two major parts. The first set of manipulations involved putting together a general vector (designated as EL301) for plant gene expression that incorporates the omega sequence of the Tobacco Mosaic Virus leader sequence into the 5' region of the desired transcript. As previous work by Gallie et al. (1987) have shown, this should substantially increase the translation efficiency of the RNA of interest. The second part consisted of the insertion of the synthetic bO gene (Nassal et al. 1987) fused to a sequence encoding the chloroplast-targeting transit peptide from the soybean Cab3 gene (Walling et al. 1988) into the polylinker sites that are present in our general expression vector EL103. The resultant vector was designated as EL301. The following is a detailed description of the steps involved.

Part 1: Construction of the General Expression Vector for Foreign Protein Production in Higher Plants a. The Omega sequence of TMV was amplified from pJII103 (Gallie et al. 1987) by PCR using two primers:

EL174 5'-GCTCTAGATATTTTTACAACAATTACC-3'
EL175 5'-CGATCCGGATCCTGTCTCTTGA-3'

These primers introduce an Xba1 site immediately upstream from the Omega sequence and a BamHI site down stream from the 3' end of Omega. These are underlined in EL174 and EL175, respectively.

b. The amplified fragment was digested with the restriction enzymes XbaI and BamHI and was then subcloned into the vector pBI121 (purchased from Clontech Co.) at the same sites. This places the Omega sequence between the 35S promoter of CaMV (cauliflower mosaic virus) and the β-glucurondiase (GUS) reporter gene. A unique HindIII site is present upstream of the 35S promoter while an SstI site is present downstream of the GUS gene.

c. The XbaI site was then removed by blunting with Klenow fill-in after digestion with Xba1. The polylinker region in the pBluescript II SK (Stratagene) enclosed by BamHI and SstI sites were then used to replace the GUS gene sequence using the BamHI and SstI restriction sites, giving rise to a construct called pZM24. This effectively replaced the GUS gene with a polylinker region containing the restriction sites BamHI, SpeI, Xba1, NotI, SacII and SstI.

d. The HindIII/EcoRI fragment (35S promoter-Omega-nos 3' terminator) from pZM24 was then exchanged with the 35S-GUS-nos 3' sequence in pBI121 (purchased from Clontech Co.). The vector pBI121 is derived from pBIN19 which is a disarmed Agrobacterium vector that allows for plant transformation via this soil bacterium (Bevan, 1984). The final vector, designated as EL103, contains three unique restriction sites located between the Omega sequence and the Nos-3' terminator sequence from the nopaline synthase gene of the Agrobacterium T-DNA.

Part 2. Amplification of the Cab3 Transit Peptide from Soybean Genomic DNA and Cloning of bO Gene Fusion into Expression Vector a. The genomic DNA of soybean (*Glycine max*, cv. Corsoy) was used to amplify the transit peptide from the Cab3 locus (Walling et al., 1988). The primers used were:

EL60 5'-GATCGATATGGCAGCAGCTTCTTCC-3'
EL61 5'-GAAGCTTGCTCACCCTTCCACATCC-3'

The primers were designed to insert a ClaI site and a HindIII site at the 5' and 3' portion of this transit peptide sequence, as indicated by the underlined nucleotides. After PCR under standard conditions (35 cycles of: 94° C., 1 min.; 55° C., 1 min.; 72° C., 1 min.), the amplified fragment was digested with HindIIi and ClaI. This fragment was designated as Cab-t.

b. The fragment was then ligated to a pBluescript SKII vector (cut with EcoRI/ClaI) and the bO gene plasmid from Dr. Knorana (cut with HindIII/EcoRI). The resultant fusion, designated as Cab-bO, between the Cab-t sequence and bO was confirmed by sequence analysis. A single base difference was found in our PCR product from that of the published Cab3 sequence. This changed a valine amino acid upstream from the predicted processing site into a cysteine residue.

c. The ClaI/SstI fragment containing the Cab-t/bO fusion gene was isolated from our clone Cab-bO and inserted into EL103. The ClaI site was blunted by Klenow fill-in and then the fragment isolated from Cab-bO after SstI digestion. This was subcloned into EL103 vector that has been cut with BamHI, filled-in with Klenow and then digested with SstI. The resultant clone is designated as EL301. This is a construct for overexpression of bO in higher plants.

Expression of bO in *Arabidopsis thaliana* also Result in Spontaneous Lesions and Induction of Defense Responses The construct EL301, described above, has been introduced into Arabidopsis thaliana (ecotype RLD) by Agrobacterium-mediated transformation. The transformed plants showed spontaneous lesions in mature rosette leaves that exhibited similar morphology to those observed with our transgenic tobacco plants. Furthermore, when examined by fluorescence microscopy, they showed UV-fluorescent material in and around these lesion sites. This is similar to those observed in lesions arising from an incompatible interaction between plants containing resistance genes and pathogens containing the corresponding avirulence genes (Greenberg et al., 1994). We have also determined the level of the major phytoalexin of Arabidopsis, called camalexin, in these transgenic plants containing the construct EL301. We found an approximately 3 to 4 fold increase in camalexin levels in transgenic leaves without visible lesions. In leaves showing a large number of spontaneous lesions, we observe about a 100 fold increase in camalexin levels. Since phytoalexins are antimicrobial compounds, it is expected that this overproduction should lead to significant increase in resistance to bacterial and fungal pathogens. The salicylic acid (abbreviated as SA) content of our transgenic plants has been determined since it is believed that SA is an important signal for the induction of plant defense genes. About a 20-fold increase has been found in SA content in transgenic Arabidopsis plants that expressed spontaneous lesions in response to the expression of bO. These results are consistent with expectation that bO expression can be used in divergent plant species to induce the latent defense responses that are normally activated only upon an incompatible interaction.

Testing the Effects of bO Expression in Monocots

Genetic mutants from certain monocot plant species, such as maize and barley, have been characterized which showed a disease lesion mimic phenotype. One such locus of barley, called mlo, shows heightened resistance to fungal pathogens. This is similar to that observed with some of the lesion mimics found in dicots species, such as tomato and Arabidopsis. The bO transgene should induce spontaneous lesions as well as defense responses in monocots as well. The bO expression cassette is being introduced into turfgrass. The methodologies have been worked out for the construction of transgenic monocots, such as turfgrass (Hartman et al., 1994). For these species, the selection marker that will be used is the bacterial bar gene that confers resistance to Biolafos, a commercial herbicide.

The bO gene in like manner is being introduced into other monocot species, for example, maize and rice.

REFERENCES

Atkinson, M. M., and Baker, C. J. (1989). Role of the plasmalemma H+-ATPase in *Pseudomonas syringae*-induced K+/H+ exchange in suspension-cultured tobacco cells. Plant Physiol. 91, 298–303.

Bachmair, A., Becker, F., Masterson, R. V., and Schell, J. (1990). Perturbation of the ubiquitin system causes leaf curling, vascular tissue alterations and necrotic lesions in higher plants. EMBO J. 9, 4543–4549.

Becker, F., Buschfeld, E., Schell, J., and Bachmair, A. (1993). Altered response to viral infection by tobacco plants perturbed in ubiquitin system. Plant J. 3, 875–881.

Bevan, M. (1984). Binary Agrobacterium vectors for plant transformation. Nucleic Acids Res. 12:8711–8721.

Bowles, D. J. (1990). Defense-related proteins in higher plants. Annu. Rev. Biochem. 59, 873–907.

Dietrich, R. A., Delaney, T. P., Uknes, S. J., Ward, E. R., Ryals, J. A., and Dangl, J. L. (1994). Arabidopsis Mutants Simualting Disease Resistance Response. Cell 77, 565–577.

Elkind, H., Edwards, R., Mavandad, M., Hedrick, S. A., Ribak, O., Dixon, r. A. and Lamb, C. (1990). Abnormal plants development and down regulation of phenylpropanoid biosynthesis in transgenic tobacco containing a heterologous phenylalanine ammonia-lyase gene. Proc. Natl. Acad. Sci. 87, 9057–9061.

Enyedi, A. J., Yalpani, N., Silverman, P., and Raskin, I. (1992). Signal molecules in systemic plant resistance to pathogens and pests. Cell 70, 879–886.

Fraley, R. T., Rogers, S. G., Horsch, R. B., Eichholz, D. A., Flick, J., Fink, C. L., Hoffman, N. L., and Sanders, P. R. (1985). The SEV system: a new disarmed Ti plasmic vector system for plant transformation. Bio/Technology 3, 629–635.

Gallie, D. R., Sleat, D. E., Watts, J. W., Turner, P. C. and Wilson, T. M. A. 1987). The 5'-leader sequence of tobacco mosaic virus RNA enhances the expression of foreign gene transcripts in vitro and in vivo. Nucleic Acids Rers. 15:3257–3273.

Greenberg, J. T., and Ausubel, F. M. (1993). Arabidopsis mutants compromised for the control of cellular damage during pathogenesis and aging. Plant J. 4, 327–342.

Greenberg, J. T., Ailan, G., Klessig, D. F., and Ausubel, F. M. (1994). Programmed cell death in plants: A pathogen-triggered response activated coordinately with multiple defence functions. Cell 77: 551–563.

Hartman, C. L., Lee, L., Day, P. R., and Tumer, N. E. (1994). Herbicide Resistant Turfgrass (*Agrostis palustris Huds.*) by Biolistic Transformation. Bio/Technology 12, 919–923.

Hoisington, D. A., Neuffer, M. G., and Walbot, V. (1982). Disease lesion mimic in maize. Dev. Biol. 93: 381–388.

Krebs, M. P., and Khorana, H. G. (1993). Mechanism of light-dependent proton translocation by bacteriorhodopsin. J. Bacterio. 175, 1555–1560.

Lamb, C. J. (1994). Plant disease resistance genes in signal perception and transduction. Cell 76, 419–422.

Lawton, K., Uknes, S., Friedrich, L., Gaffney, T., Alexander, D., Goodman, R., Metraux, J. P., Kessman, H., Ahl-Goy, P., Gutrella, M. Ward, E., and Ryals, J. (1993). The molecular biology of systemic acquired resistance. In Mechanisms of Plant Defence Responses, B. Fritig and M. Legrand, eds. (Netherlands, Kluwer Academic Publishers), pp. 422–432.

Linthorst, J. M. (1991). Pathogenesis-related proteins of plants. Critical Rev. Plant Sci. 10, 123–150.

Malamy, J., Carr, J. P., Klessig, D. F., and Raskin, I. (1990). Salicylic acid: a likely endogenous signal in the resistance response of tobacco to viral infection. Science 250: 1002–1004.

Malamy, J., Henning, J., and Klessig, D. F. (1992). Temperature-dependent induction of salicylic acid and its conjugates during the resistance response to tobacco mosaic virus infection. Plant Cell 4, 359–366.

Metraux, J. P., Singer, H., Rayals, J., Ward, E., Wyss-Benz, M., Gaudin, J., Raschdorf, K., Schmid, E., Blum, W., and Inverardi, B. (1990). Increase in salicylic acid at the onset of systemic acquired resistance in cucumber. Science 250, 1004–1006.

Nagy, F., Boutry, M., Hsu, M-Y., Wong, M., and Chua, N-H. (1987). The 5'-proximal region of the wheat-1 gene contains a 268-bp enhancer-like sequence for phytochrome response. EMBO J. 6, 2537–2542.

Nassal, M., Mogi, T., Karnik, S. S., and Khorana, H. G. (1987). Structure-function studies on bacteriorhodopsin J. Biol. Chem. 262, 9264–9270.

Neuffer, M. G., and Calvert, O. H. (1975). Dominant lesion mimics in maize. J. Hered. 66, 265–270.

Otto, H., Marti, T., Holz, M., Mogi, T., Stern, L. J., Engel, F., Khorana, H. G., and Heyn, M. P. (1990). Substitution of amino acids Asp-85, Asp-212 and Arg-82 in bacteriorhodopsin affects the proton release phase of the pump and the pK of the Schiff base. Proc. Natl. Acad. Sci. USA 87, 1018–1022.

Pryor, A. (1987). The origin and structure of fungal disease resistance genes. Trends Genet. 3, 157–161.

Ross, A. F. (1961). Systemic acquired resistance induced by localized virus infection in plants. Virology 14, 340–358.

Takahashi, H., Shimamoto, K. and Ehara, Y. (1989). Cauliflower mosaic virus gene VI causes growth suppression, development of necrotic spots and exprsesion fo defence-related genes in transgenic tobacco plants. Mol. Gen. Genet. 216, 188–194.

Walbot, V., Hoisington, D. A., and Neuffer, M. G. (1983). Disease lesion mimics in maize. In Genetic Engineering of Plants, T. Kosuge and C. Meredith, eds. (New York: Plenum Publishing Company), pp. 431–442.

Walbot, V. (1991). Maize mutants for the 21st century. Plant Cell 3, 851–856.

Walling, L. L., Chang, Y. C., Demmin, S., and Holzer, F. M. (1988). Isolation, characterization and evolutionary relatedness of three members from the soybean multigene family encoding chlorophyll a/b binding proteins. Nucleic Acids Res. 16:10477–10492.

Ward, E. R., Uknes, S. J., Williams, S. C., Dincher, S. S., Widerhold, D. L., Alexander, D. C., Ahl-Goy, P., Metraux, J-P., and Ryals, J. A. 91991). Coordinate gene activity in response to agents taht induce systemic acquired resistance. Plant Cell 3, 1085–1094.

Wolter, M., Hollricher, K., Salamini, F., and Shulze-Lefert, P. (1993). The mlo resistance alleles to powdery mildew infection in barley trigger a developmentally controlled defence mimic phenotype. Mol. Gen. Genet. 239, 122–128.

Yalpani, N., Shulaev, V., and Raskin, I. (1993). Endogenous salicylic acid levels correlate with accumulation of pathogenesis-related proteins and virus resistance in tobacco. Phytopathol. 83, 702–708.

What is claimed is:

1. A transgenic plant cell which is transformed with and expresses a gene encoding bacterio-opsin, or the progeny of said cell.

2. A transgenic plant cell of claim 1 wherein the plant is a dicot species.

3. A transgenic plant cell of claim 1 wherein the plant is a monocot species.

4. A transgenic plant, the cells of which express a gene encoding bacterio-opsin, or the progeny of said plant.

5. A transgenic plant of claim 4 which is a dicot species.

6. A transgenic plant of claim 4 which is a monocot species.

7. A method for enhancing resistance of a higher plant to attack by one or more plant pathogens by transforming said plant with a gene encoding bacterio-opsin.

8. A method of claim 7 wherein the plant is a dicot species.

9. A method of claim 7 wherein the plant is a monocot species.

10. A method of claim 7 wherein the cells of said plant were transformed using a binary bacteria-opsin gene vector.

11. The method of claim 10 wherein the binary bacterio-opsin gene vector is EL-301.

12. The method of claim 10 wherein said vector is derived from EL-301 by replacing the 35S promoter with a promoter that is activated upon pathogen attack.

13. The method of claim 10 wherein said vector is RM-102.

14. The method of claim 10 wherein said vector is derived from RM-102 by replacing the 35S promoter with a promoter that is activated upon pathogen attack.

15. A bacterio-opsin gene vector comprising a nucleotide sequence encoding bacterio-opsin and regulatory elements for the expression of bacterio-opsin in plant cells.

16. The vector of claim 15 wherein said bacterio-opsin gene vector is EL-301.

17. The vector of claim 16 wherein the 35S promoter is replaced with a promoter that is activated upon pathogen attack.

18. The vector of claim 15 wherein said bacterio-opsin gene vector is RM-102.

19. The vector of claim 18 wherein the 35S promoter is replaced with a promoter that is activated upon pathogen attack.

20. The vector according to claim 15 wherein said regulatory elements are selected from the group consisting of the 35S promoter from cauliflower mosaic virus, an inducible promoter, the omega translation enhancer sequence, and the nopaline synthase termination signal.

* * * * *